United States Patent
Lee

(10) Patent No.: US 11,045,613 B2
(45) Date of Patent: Jun. 29, 2021

(54) DETECTION DEVICE FOR RECOGNIZING THE EPIDURAL SPACE

(71) Applicant: SAEUM MEDITEC CO., LTD, Bucheon-si (KR)

(72) Inventor: Ye-Jung Lee, Seoul (KR)

(73) Assignee: SAEUM MEDITEC CO., LTD, Bucheon-si (KR)

( * ) Notice: Subject to any disclaimer, the term of this patent is extended or adjusted under 35 U.S.C. 154(b) by 165 days.

(21) Appl. No.: 16/166,363

(22) Filed: Oct. 22, 2018

(65) Prior Publication Data

US 2019/0060584 A1 Feb. 28, 2019

Related U.S. Application Data

(63) Continuation of application No. PCT/KR2017/001451, filed on Feb. 10, 2017.

(30) Foreign Application Priority Data

Apr. 25, 2016 (KR) .................. 10-2016-0050093

(51) Int. Cl.
*A61M 5/46* (2006.01)
*A61M 25/01* (2006.01)
(Continued)

(52) U.S. Cl.
CPC .............. *A61M 5/46* (2013.01); *A61B 5/061* (2013.01); *A61B 5/4839* (2013.01);
(Continued)

(58) Field of Classification Search
CPC .......... A61M 5/46; A61M 5/06; A61M 5/34; A61M 39/10; A61M 25/0014;
(Continued)

(56) References Cited

U.S. PATENT DOCUMENTS 5,725,504 A * 3/1998 Collins .............. A61B 17/3401
604/117
2011/0054353 A1 3/2011 Hulvershorn et al.
(Continued)

FOREIGN PATENT DOCUMENTS

JP 2005-524435 A 8/2005
KR 101559740 B1 10/2015

OTHER PUBLICATIONS

International Search Report dated May 15, 2017.

*Primary Examiner* — Amber R Stiles
*Assistant Examiner* — Alexandra Lalonde
(74) *Attorney, Agent, or Firm* — Dinsmore & Shohl LLP; Yongsok Choi, Esq.

(57) ABSTRACT

A detection device for recognizing the epidural space is provided. The detection device includes an upper case having a predetermined shape and a lower case coupled to the upper case to form a predetermined space part. A connection tube is provided at a predetermined position of the space part, one end of the connection tube communicates with a paracentesis needle part and the connection tube communicates with a pressure sensor for measuring pressure at a predetermined position of an outer peripheral part thereof. When the paracentesis needle part reaches the epidural space, the device allows a medicine injection catheter to be inserted into the connection tube thereby reaching the epidural space, with the connection tube and the paracentesis needle part connected to each other.

8 Claims, 9 Drawing Sheets

(51) Int. Cl.
*A61M 25/00* (2006.01)
*A61M 25/06* (2006.01)
*A61B 5/00* (2006.01)
*A61B 5/06* (2006.01)
*A61B 17/34* (2006.01)
*A61B 90/00* (2016.01)
*A61B 17/00* (2006.01)

(52) U.S. Cl.
CPC .......... *A61B 5/4896* (2013.01); *A61B 5/6849* (2013.01); *A61B 5/6885* (2013.01); *A61B 17/3401* (2013.01); *A61M 25/00* (2013.01); *A61M 25/0084* (2013.01); *A61M 25/01* (2013.01); *A61M 25/06* (2013.01); *A61B 17/3494* (2013.01); *A61B 2017/00022* (2013.01); *A61B 2090/064* (2016.02); *A61M 2025/0089* (2013.01); *A61M 2205/18* (2013.01); *A61M 2205/3327* (2013.01); *A61M 2205/3344* (2013.01); *A61M 2205/50* (2013.01); *A61M 2205/502* (2013.01); *A61M 2205/587* (2013.01); *A61M 2205/8206* (2013.01); *A61M 2210/1003* (2013.01)

(58) Field of Classification Search
CPC .. A61M 25/0084; A61M 25/01; A61M 25/06; A61M 2025/0089; A61M 2210/1003; A61M 2205/18; A61M 2205/3327; A61M 2205/3344; A61M 2205/50; A61M 2205/502; A61M 2205/587; A61M 2205/8206; A61B 17/3401; A61B 2090/065; A61B 2090/064; A61B 2090/062; A61B 5/036; A61B 5/065; A61B 5/4821; A61B 5/4896; A61B 5/061; A61B 8/0833; A61B 1/00137; A61B 2017/3419

See application file for complete search history.

(56) References Cited

U.S. PATENT DOCUMENTS

| 2011/0060229 A1* | 3/2011 | Hulvershorn | A61B 5/0215 600/486 |
| 2011/0298628 A1* | 12/2011 | Vad | A61B 17/3401 340/665 |
| 2015/0119702 A1* | 4/2015 | Mulumudi | A61B 5/061 600/424 |
| 2017/0266429 A1* | 9/2017 | Striggow | A61M 5/142 |

* cited by examiner

DETECTION DEVICE FOR RECOGNIZING THE EPIDURAL SPACE

CROSS-REFERENCE TO RELATED APPLICATION(S)

This application is a continuation of International Application No. PCT/KR2017/001451 filed on Feb. 10, 2017 which claims priority to Korean Patent Application No. 10-2016-0050093 filed on Apr. 25, 2016, the entire contents of which are herein incorporated by reference.

TECHNICAL FIELD

The present invention relates to a detection device for recognizing an epidural space, more particularly, to a detection device for recognizing the epidural space which has a pressure sensor capable of accurately recognizing a pressure change in the epidural space for increasing a success rate of spine neuroplasty and spinal nerve block, and which allows to inject medicine without separating a paracentesis needle from the detection device.

BACKGROUND

The most common area of pain for South Koreans is a spine-related area. It is reported that about 3 out of 10 pain patients suffer from back pain because spinal disease is common due to sedentary lifestyles. It is known that 9 out of 10 people have had back pain at least once in a lifetime. As such, spinal disease is considered to be a very common disease, and the number of patients with spinal disease is increasing steadily.

In spinal diseases, a surgical treatment is necessary if severe pain continues due to nerve injury. However, according to the current trend, in case of simple back pain or if the back pain has just started, a non-surgical treatment such as spine neuroplasty or spinal nerve block is given. According to the statistical data, about 10% of the total patients undergo a surgical treatment and it is reported that most patients get better with a non-surgical treatment alone.

Spine neuroplasty and spinal nerve block, which are representative examples of non-surgical spine treatment, are non-surgical treatments performed by inserting a 1.7-mm diameter thin catheter (Racz catheter) in the epidural space, which is a very narrow gap surrounding the spinal nerve, and injecting a medicine to reduce inflammation and swelling around the painful nerve and thereby to induce a normal response of the autonomic nervous system.

In the non-surgical treatments, spine neuroplasty and spinal nerve block, an important criterion for measuring the success of the procedure is whether a 1.7-mm thin medical catheter inserted into the human body to administer the therapeutic medicine accurately reaches the epidural space surrounding the damaged nerve in the spine.

Generally known procedures for identifying the epidural space include a subjective procedure in which the epidural space is recognized by a subjective feeling transmitted to the clinician's fingertips when a paracentesis needle passes through the ligamentum flavum, a loss of resistance method using air or a saline solution, and a paracentesis under ultrasound guidance.

The loss of resistance method to identify the epidural space, which is most commonly used to perform neuroplasty and spinal nerve block in pain clinics and pain specialist hospitals, is a one-dimensional method, in which a syringe is filled with air or a saline solution and a needle punctures and is advanced into the part of the spine to be treated. In this method, if the air or the saline solution is not lost when a piston of the syringe is pushed during the advance of the needle, it is determined that the resistance exists because the needle stays on the muscle layer. If the air or the saline solution in the syringe is discharged and lost when the piston of the syringe is pushed during the advance of the needle, it is determined that the resistance does not exist because the needle has reached the gap, epidural space.

The loss of resistance method is most widely used for recognizing the epidural space due to the simplicity of the procedure. However, it has a problem that the clinician's recognition of a sudden loss of the resistance against the air or fluid in a syringe cannot accurately confirm whether the needle has reached the epidural space. That is, in the case of a patient whose ligamentum flavum, which is located anterior to the epidural space, is not closed at the median part, there is no feeling that the paracentesis needle passes through the ligamentum flavum, so that the paracentesis needle passes through the epidural space to reach the spinal cord. Also, in the elderly or patients with congenital deformity of the interspinous ligaments, there is a gap, like the epidural space, between the muscle layers as a result of cavity formation due to degeneration of the interspinous ligaments, leading to the error of confusing this gap with the epidural space.

In order to solve the above problems, Korean Patent No. 1,559,740 discloses an epi check point that is digitally operated, which comprises a dura pressure sensor part for directly receiving and measuring a biometric pressure signal generated from each of the muscles and the epidural space in the human body by contacting them while electrically insulated, detecting the respective differences in pressure, converting the differences into digital electrical signals and outputting them; a dura pressure difference amplification part for receiving levels of the signals detected by the dura pressure sensor part and digitally amplifying the signals at a predetermined amplification rate; a dura pressure comparison part for receiving the amplified signals and the amplification rate from the dura pressure difference amplification part, comparing the signals with a reference signal stored correspondingly to the amplification rate by a digital signal processing, determining which one is larger, and outputting the comparison result; a dura pressure latch part for receiving and storing the digital signal output from the dura pressure comparison part; and a dura pressure display part for emitting either green light or red light according to the signal output from the dura pressure latch part.

According to the prior art as described above, in order to inject a medicine into the epidural space, a dura pressure detection housing part and a needle for anesthesia of the cervical vertebrae need to be separated from each other, and then a syringe for injecting a medicine needs to be connected to the needle for anesthesia of the cervical vertebrae. However, when separating the needle for anesthesia of the cervical vertebrae from the dura pressure detection housing part or connecting the needle for anesthesia of the cervical vertebrae, cases may often occur where the position of the needle for anesthesia of the cervical vertebrae moves due to a fluctuation resulting from an external force, so that the needle deviates from the epidural space which is only a few millimeters wide.

SUMMARY

The present invention has been made to solve the above problems. An object of the present invention is to provide a detection device for recognizing the epidural space, which is capable of accurately recognizing the epidural space and allows to inject a medicine even when a paracentesis needle and the detection device is not separated from each other, during spine neuroplasty or spinal nerve block.

Another object of the present invention is to provide a detection device for recognizing the epidural space with improved ease of use, which promptly notifies whether a paracentesis needle has reached the epidural space so that the user can easily recognize it.

Another object of the present invention is to provide a detection device for recognizing the epidural space, which provides a function of determining whether a medicine injection catheter has accurately reached a position determined by a preliminary examination, after recognizing the epidural space.

In order to achieve the above objects, the detection device for recognizing the epidural space according to the present invention comprises: an upper case 100 having a predetermined shape; and a lower case 200 coupled to the upper case 100 to form a predetermined space part 220, wherein a connection tube 500 is provided at a predetermined position of the space part 220, one end of the connection tube 500 communicating with a paracentesis needle part 700 and the other end thereof having a detachable cap part 510, and an opening 530 in communication with a pressure sensor 400 for measuring pressure being provided at a predetermined position of an outer peripheral part thereof, and wherein, when a paracentesis needle part 700 reaches the epidural space, the device allows a medicine injection catheter 1000 to be inserted into the connection tube 500 thereby reaching the epidural space, with the connection tube 500 and the paracentesis needle part 700 connected to each other.

In addition, the upper case 100 has fixing protrusions 130 for fixing the paracentesis needle part 700. The lower case 200 has a fixing groove part 210 for fixing and accommodating the needle part 700. The space part 220 may further have a PCB substrate 300 having a program embedded therein for calculating a result of the pressure sensor 400.

The PCB substrate 300 may further have an LED lamp 310 for indicating the calculation result value of the pressure sensor 400.

Further, the PCB substrate 300 may further have a travel distance sensor 330 capable of sensing a travel distance of the medicine injection catheter 1000.

Further, the PCB substrate 300 may further have a LCD display window 320 for informing a result of the travel distance sensor 330.

Further, a power button 110 and a reset button 120 may be further provided on one side of the upper case 100.

Further, the upper case 100 may be made of a diffusion PC.

Further, one end and the other end of the connection tube 500 may protrude from the space part 220 of the upper case 100 and the lower case 200.

Further, an outer expansion part 520 may be further provided on an outer surface of one end of the connection tube 500 to be connected to the needle part 700.

Here, it is preferable that the outer expansion part 520 is made of an elastic body.

The detection device for recognizing the epidural space according to the present invention can accurately recognize the epidural space because it has a pressure sensor. Further, it allows a medicine injection catheter to be inserted into the epidural space without separating a paracentesis needle from the detection device, thereby increasing the possibility of success of neuroplasty or nerve block.

In addition, the detection device for recognizing the epidural space according to the present invention may have an element allowing an outer expansion at the engagement part to be connected to the paracentesis needle. Thus, paracentesis needles having different inner diameters can be used with a single detection device, which greatly enhances the usability of the detection device.

Further, the detection device for recognizing the epidural space according to the present invention may have a travel distance sensor that can accurately identify the travel distance and position of the medicine injection catheter, which enables a medicine to be injected to a desired position.

Further, the detection device for recognizing the epidural space according to the present invention may have an LED lamp and an LCD display window, which allow a user to quickly identify whether a paracentesis needle has reached the epidural space and also identify the travel distance of the medicine injection catheter.

DETAILED DESCRIPTION

Hereinafter, the detection device for recognizing the epidural space according to the present invention will be described with reference to the accompanying drawings.

As used herein, the terms "comprise", "have" and "provided" are intended to express the presence of the features, numbers, steps, elements, parts or combinations thereof. It is not to be understood that the terms are to exclude possible presence or addition of one or more other features, numbers, steps, actions, elements, parts or combinations thereof.

Also, unless otherwise defined, all terms used herein, including technical or scientific terms, have the same meaning as commonly understood by those skilled in the art to which the present invention belongs. Terms such as those defined in commonly used dictionaries are to be interpreted as having a meaning consistent with the meaning of the context in the relevant art and are not to be interpreted in an ideal or overly formal sense unless expressly defined herein.

Figure 1:
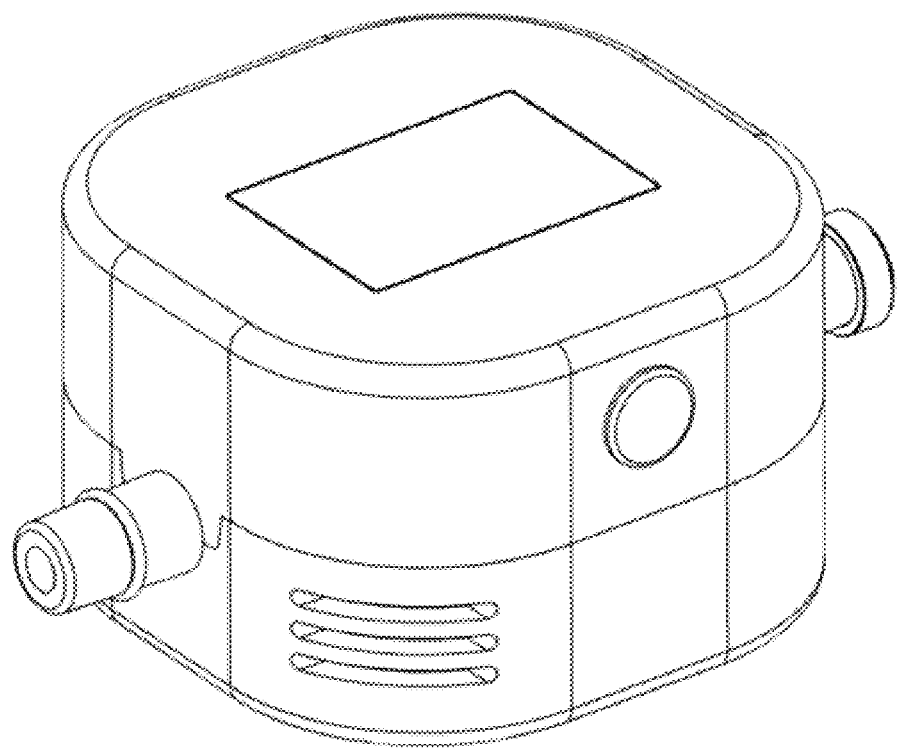
FIG. 1 is a photograph of the exterior of the detection device for recognizing the epidural space of the present invention.

FIG. 1 is a photograph of the exterior of the detection device for recognizing the epidural space according to one embodiment of the present invention. Each of FIGS. 2A and 2B is a photograph of the exterior of the detection device for recognizing the epidural space of the present invention having a paracentesis needle (a spine needle in FIG. 2A, an epidural needle in FIG. 2B) attached thereto.

Figure 2A:
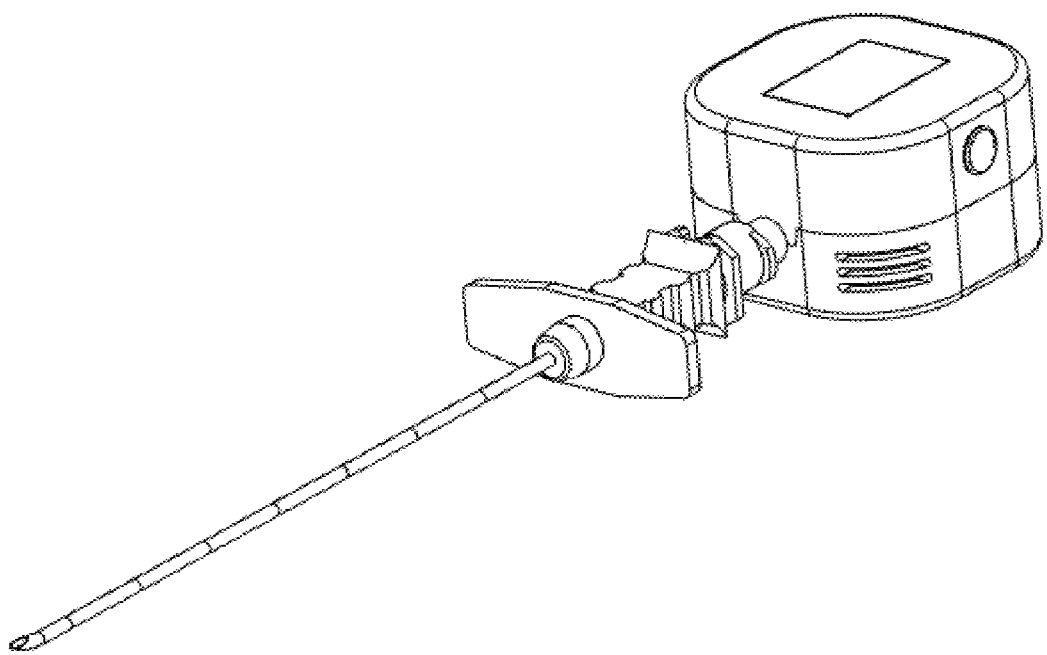
FIG. 2A is a photograph of the exterior of the detection device for recognizing the epidural space of the present invention having a spine needle attached thereto.
Figure 2B:
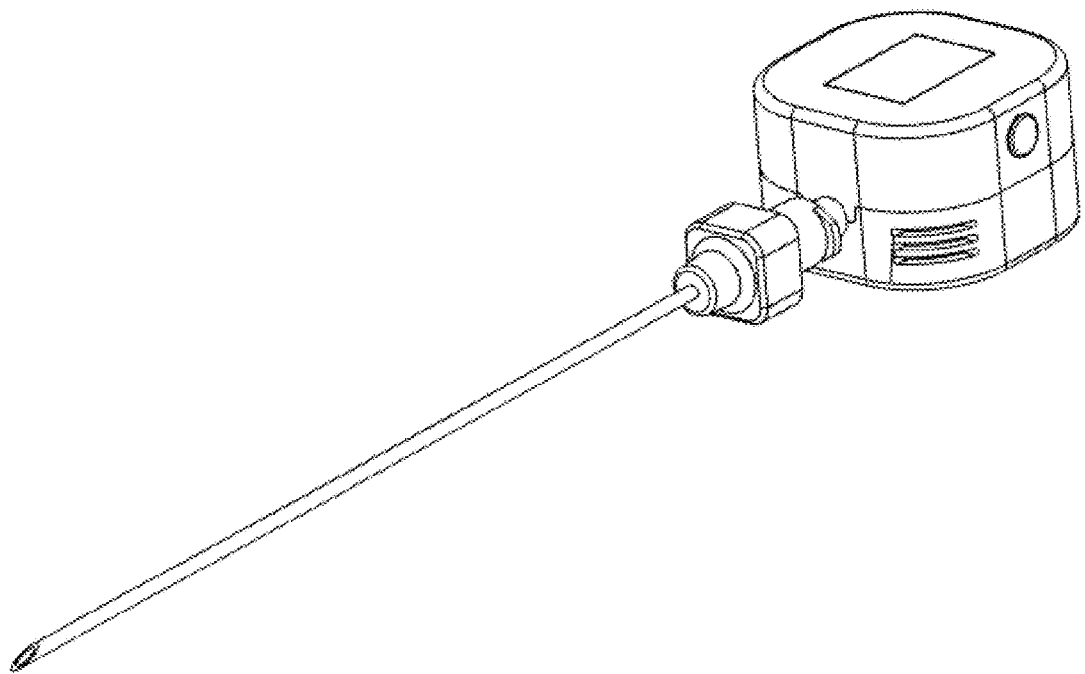
FIG. 2B is a photograph of the exterior of the detection device for recognizing the epidural space of the present invention having an epidural needle attached thereto.

That is, the detection device for recognizing the epidural space of the present invention is a medical device used for locating the epidural space in a state where a spine needle or an epidural needle, which are paracentesis needles, is combined therewith, as shown in FIGS. 2A and 2B.

Figure 3:
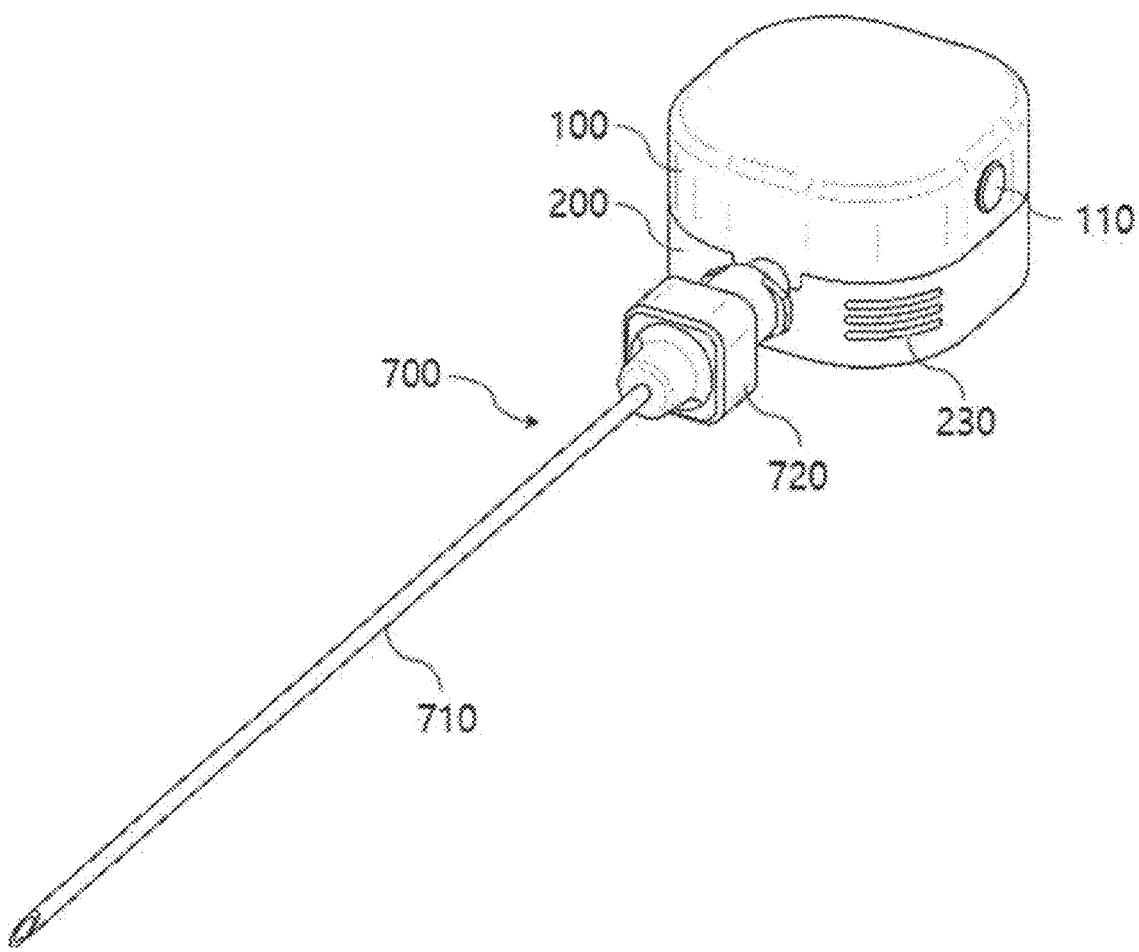
FIG. 3 is a perspective view of the detection device for recognizing the epidural space of the present invention having a paracentesis needle attached thereto.

FIG. 3 is a perspective view of the detection device for recognizing the epidural space of the present invention having a paracentesis needle attached thereto.

Figure 4:
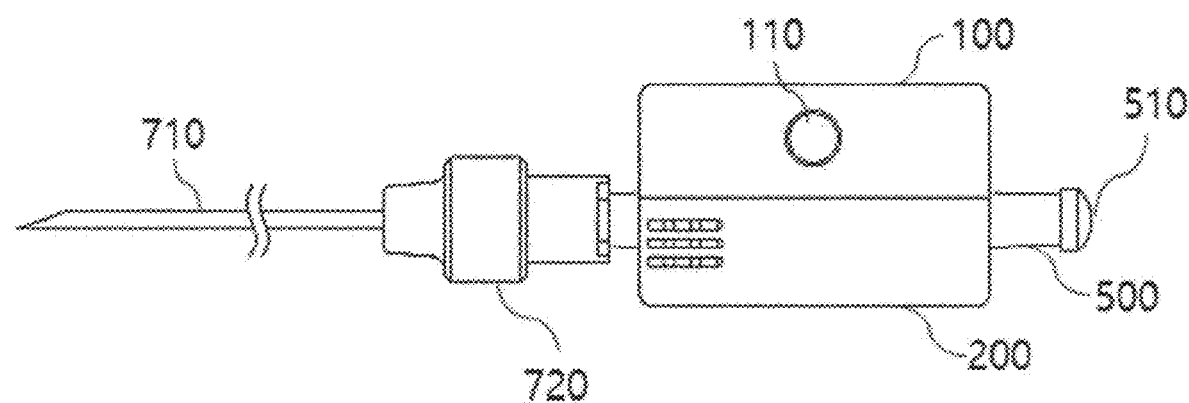
FIG. 4 is a side view of the detection device for recognizing the epidural space of the present invention having a paracentesis needle attached thereto.
Figure 5:
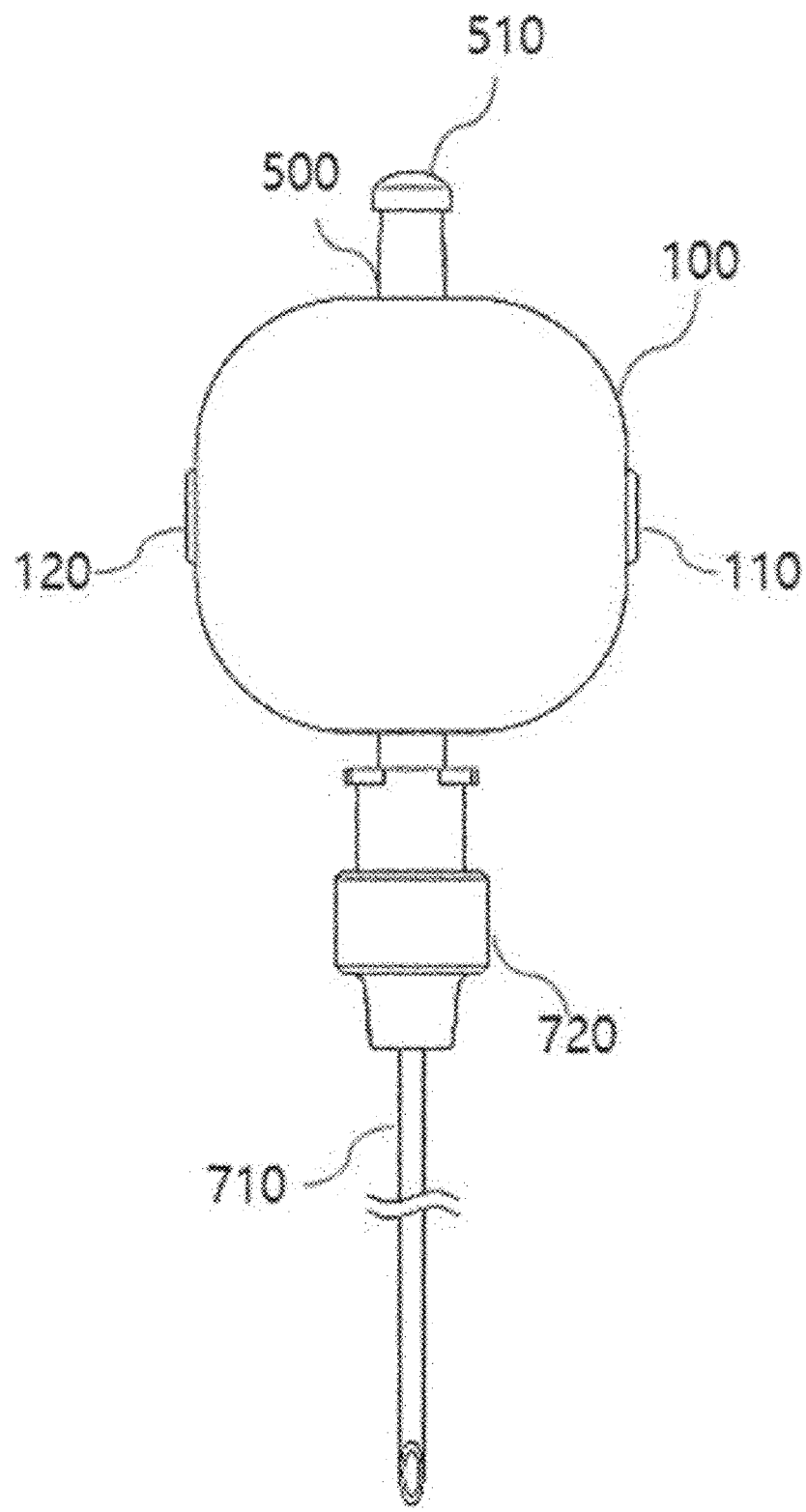
FIG. 5 is a plan view of the detection device for recognizing the epidural space of the present invention having a paracentesis needle attached thereto.
Figure 6:
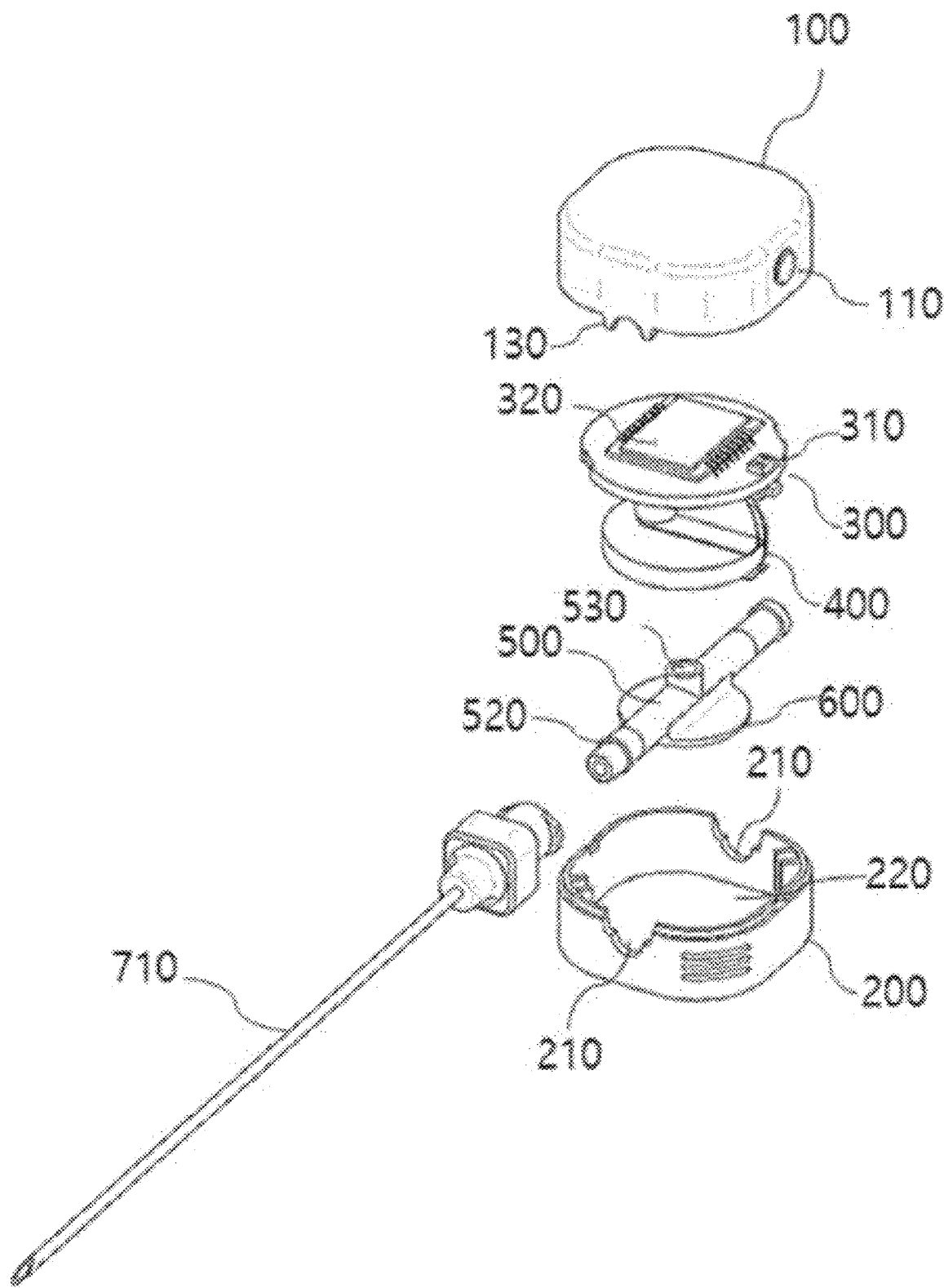
FIG. 6 is an exploded view of the perspective view of FIG. 3.
Figure 7:
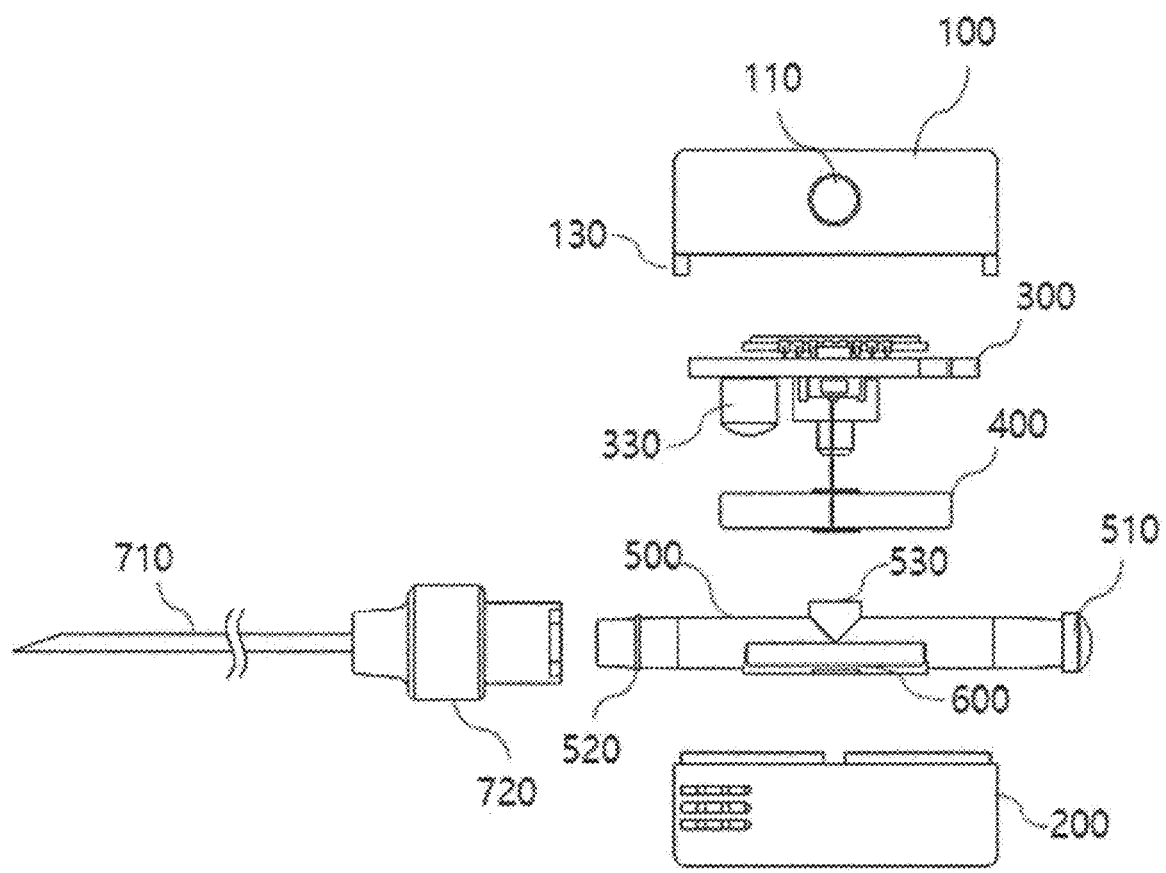
FIG. 7 is an exploded view of the side view of FIG. 4.
Figure 8:
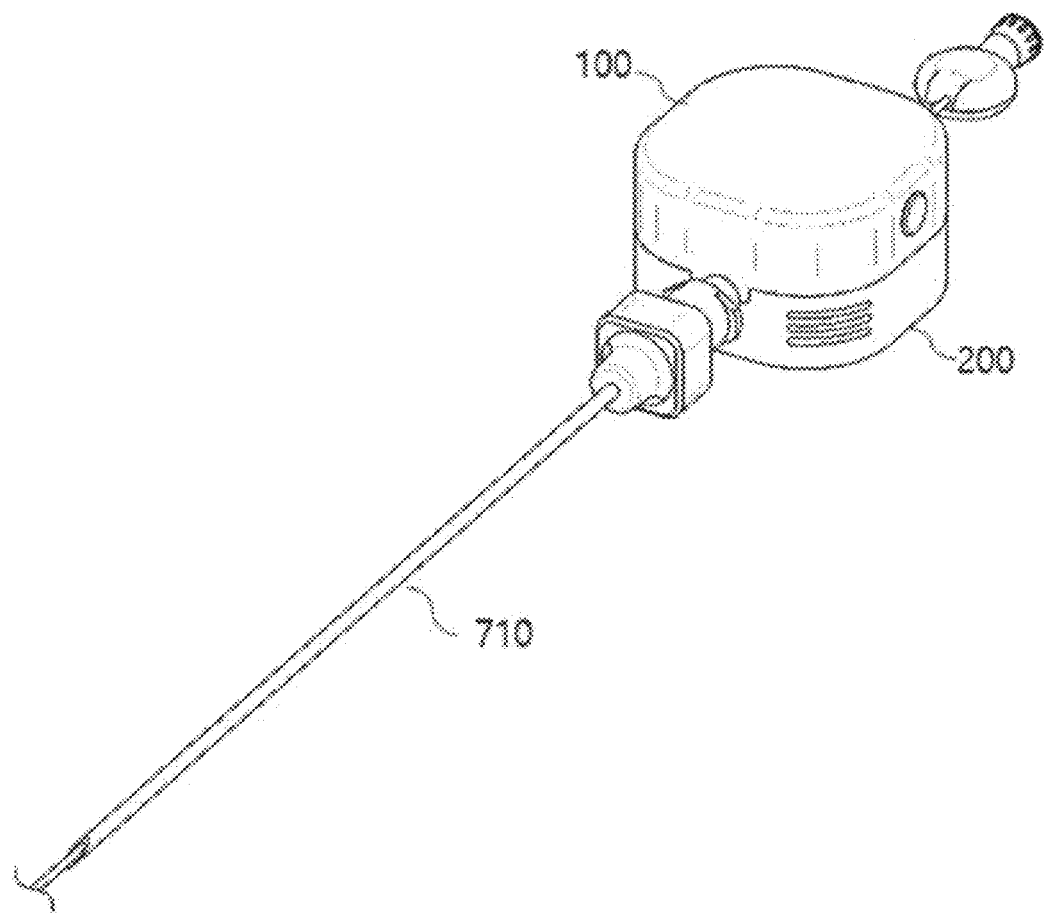
FIG. 8 is a perspective view of the detection device for recognizing the epidural space of the present invention, in which the medicine injection catheter has been inserted in a state where a paracentesis needle is attached.
Figure 9:
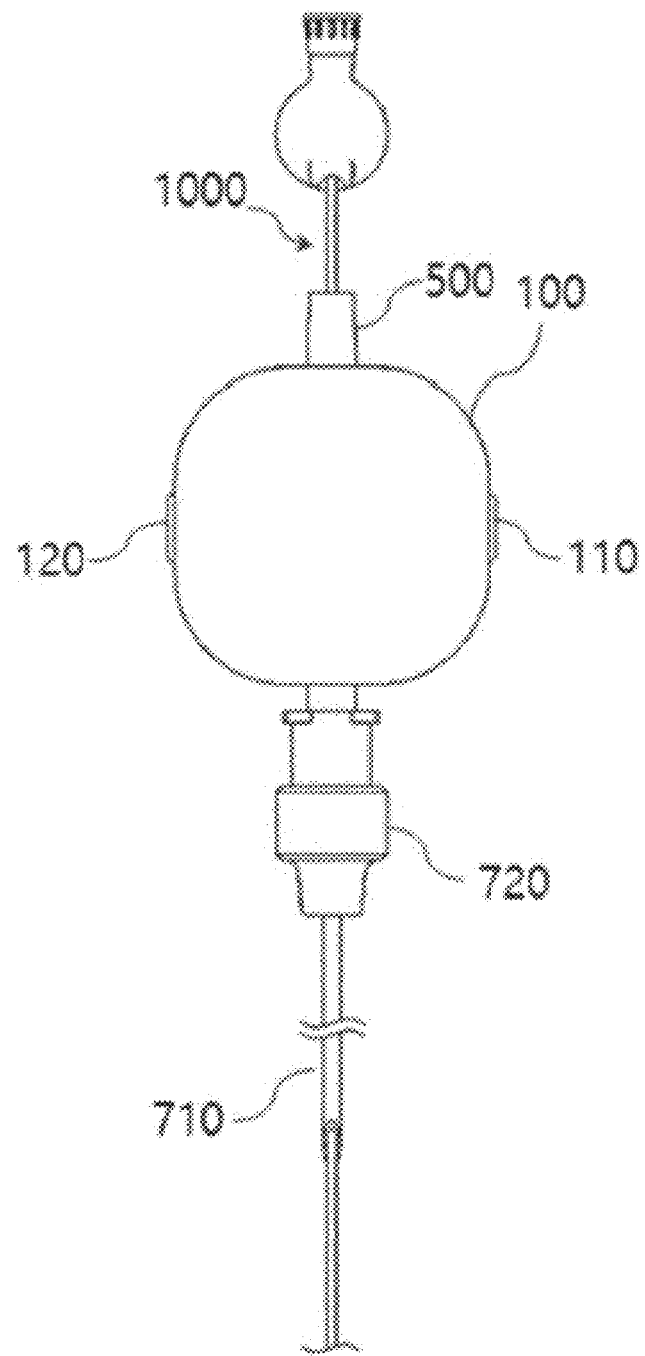
FIG. 9 is a plan view of FIG. 8.

FIG. 4 is a side view of FIG. 3. FIG. 5 is a plan view of FIG. 3. FIG. 6 is an exploded view of the perspective view of FIG. 3. FIG. 7 is an exploded view of the side view of FIG. 4.

As can be seen from the drawings, the detection device for recognizing the epidural space of the present invention comprises an upper case 100 having a predetermined shape and a lower case 200, and a space part 220 formed by the coupling of the upper case 100 and the lower case 200 may accommodate a PCB substrate 300, a pressure sensor 400, a connection tube 500, a battery 600, etc., which will be described below.

The upper case 100 of the detection device for recognizing the epidural space according to the present invention may have a pair of fixing protrusions 130 facing each other at predetermined positions on the outer surface thereof. The pair of fixing protrusions 130 are to stably fix a paracentesis needle part 700 to the detection device for recognition. After an engagement part 720 of the paracentesis needle part 700 is seated on the fixing groove part 210 (to be described below) of the lower case 200, the fixing protrusions 130 of the upper case 100 tightly fix the paracentesis needle part 700 from above so that the paracentesis needle part 700 is firmly coupled to the detection device for recognition.

It is preferable that a power button 110 and a reset button 120 are further provided at predetermined positions on the outer surface of the upper case 100.

The power button 110 may supply power to operate the PCB substrate 300, which supplies power and controls the pressure sensor 400, an LED lamp 310, an LCD display window 320 and so on for measuring the epidural space and the travel distance of a medicine injection catheter and notifying the user of the result The reset button 120 is to initialize the measurement value of the pressure sensor or the measurement result of the travel distance of the catheter 1000. A detailed description thereof will be given below.

The upper case 100 may be preferably made of a material that transmits light so that the result displayed by the LCD display window 320 can be easily seen from the outside, more preferably, a diffusion PC (polycarbonate) having a light diffusion function.

The lower case 200 has a shape corresponding to the upper case 100. It may have a fixing groove part 210 at a predetermined position on the edge part. As described above, the fixing groove part 210 serves to stably fix the paracentesis needle part 700, together with the fixing protrusions 130 of the upper case 100.

Further, it is preferable that a heat release hole 230 for discharging the heat generated during the operation of the PCB substrate 300, the LED lamp 310, the LCD display window 320, the travel distance sensor 330, and the pressure sensor 400 accommodated in the space part 220, is provided at a predetermined position on the outer surface of the lower case 200.

The upper case 100 and the lower case 200 of the present invention are illustrated as having a roughly tetragonal shape. However, this is just an exemplary illustration and it is obvious that the outer shape of the cases can be modified by those skilled in the art.

The space part 220 formed by the coupling of the upper case 100 and the lower case 200 may accommodate the PCB substrate 300, the LED lamp 310, the LCD display window 320, the travel distance sensor 330, the pressure sensor 400, the connection tube 500, and the battery 600.

Hereinafter, the connection tube 500, which is one of the major elements of the present invention, will be described in detail with reference to FIG. 6 and FIG. 7.

The connection tube 500 accommodated in the space part 220 may have a long cylindrical shape which has a predetermined inner diameter, and both ends and a predetermined position of the outer peripheral part of which are open.

The inner diameter of the connection tube 500 is not particularly limited, but it is preferably within a range where the medicine injection catheter 1000 can pass through it.

One end of the connection tube 500 may horizontally communicate with the paracentesis needle part 700 and the other end thereof may have a detachable cap part 510. In addition, an opening 530 formed at a predetermined position of the outer peripheral part communicates with the pressure sensor 400 to allow measurement of the pressure at the position where the paracentesis needle is inserted.

Below a detailed explanation will be given about the pressure measurement consisting of the above elements. The paracentesis needle inserted into the skin to locate the epidural space and the connection tube 500 have been connected to each other, and the other end of the connection tube 500 has been sealed by the cap part 510. Thus, the pressure sensor 400 in communication with the opening 530 of the connection tube 500 can accurately measure the pressure at the position where the needle is inserted.

Here, the cap part 510 provided at the other end of the connection tube 500 supports measuring the pressure at the position of the paracentesis needle inserted in the human body, and injecting a medicine into the epidural space with the medicine injection catheter 1000 when the epidural space has been recognized.

That is, in order to locate the epidural space with no affection by the ambient pressure (atmospheric pressure), it is necessary to measure the pressure with the cap part 510 attached to the connection tube 500). However, after the epidural space is accurately located, the cap part 510 is detached from the connection tube 500 so that the medicine injection catheter 1000 can be inserted into the inner space of the connection tube 500.

As described above, the detection device for recognizing the epidural space of the present invention has a connection tube 500, one end of which horizontally communicates with the paracentesis needle part 700, the other end of which has a detachable cap part 510, and which has an opening 530 at a predetermined position on the outer peripheral part that communicates with the pressure sensor 400. Thus, it is possible to not only accurately locate the epidural space, but also accurately insert the medicine injection catheter 1000 into the epidural space.

In other words, in the prior art, there is no element capable of performing the same function as the connection tube 500 of the present invention. Thus, it is difficult to accurately locate the epidural space. Moreover, even if the epidural space is accurately located, it is very difficult to accurately insert the medicine injection catheter 1000 into the epidural space, because, in order to insert the medicine injection catheter 1000 into the paracentesis needle part 700, it is necessary to separate the detection device's main body from the paracentesis needle part 700 and it is highly likely that the position of the paracentesis needle part 700 will move during this process.

Meanwhile, the engagement method of the cap part 510 and the connection tube 500 is not particularly limited as long as it is a fixing method capable of detachment and attachment by a physical external force. However, preferably, it may be male and female screw engagement. Given that the movement of the detection device needs to be minimized in order to prevent movement of the needle from the epidural space, male and female screw engagement is preferred. Also, it is more preferable to have packing at the cap part 510 in order to maintain airtightness.

It is preferable that one end and the other end of the connection tube 500 protrude from the space part 220 of the upper case 100 and the lower case 200 by a predetermined length.

Since the one end is to be physically connected to the paracentesis needle part 700 and the other end is to be connected to the cap part 510, it is preferable to design the ends such that they protrude from the space part 220 by a predetermined length in order to allow easy replacement of the needle part 700 and attachment or detachment of the cap part 510.

Further, it is preferable that the outer expansion part 520 is further provided on the outer surface of one end of the connection tube 500 connected to the paracentesis needle part 700.

A spine needle 710 (or an epidural needle) is generally used as the needle for detecting the epidural space. Since the spine needle 710 and the epidural needle are different from each other in their inner diameters of the engagement part 720, conventionally, each detection device for locating the epidural space has been used for each needle. However, according to the present invention, the outer expansion part 520, with which the outer diameter can be changed, is provided at one end of the connection tube 500 to be connected to the paracentesis needle part 700 so that all the needles having different inner diameters can be used with a single detection device.

In one example, the outer expansion part 520 having a predetermined width and height may be provided at a predetermined position on the outer surface of one end of the connection tube 500, so that a needle having a smaller inner diameter may be coupled by press-fitting to the one end without the outer expansion part 520 being attached and a needle having a larger inner diameter may be connected via insertion of the outer expansion part 520.

The outer expansion part 520 is preferably made of an elastic body whose volume can be changed by an external force, although not limited thereto.

In addition, although the accompanying drawings only show the case where one outer expansion part 520 is provided, it is obvious that a plurality of outer expansion parts 520 may be provided as needed.

The pressure sensor 400 communicating with the opening 530 formed at a predetermined position on the outer peripheral part of the connection tube 500 is to identify the position of muscles, at which there is no pressure change, and the position of the epidural space, at which a pressure change occurs. The specific constitution of the pressure sensor 400 is a known technology, and thus a detailed description thereof will be omitted.

The PCB substrate 300 is provided on the top of the pressure sensor 400 and the LED lamp 310 and the LCD display window 320 are provided on the top of the PCB substrate 300. Also, a travel distance sensor 330 may be further provided between the connection tube 500 and the PCB substrate 300.

Since the pressure difference between the muscles and the epidural space of the human body is only around 5 mbar, it is necessary to amplify the electrical signal from the pressure sensor 400 in order to inform the user of the changed pressure value.

Therefore, a program for amplifying the electrical signal from the pressure sensor 400, comparing the signal with a set pressure value, and then outputting the result is embedded in the PCB substrate 300. If the measurement value of the pressure sensor 400 falls within the set pressure range, the program may perform a function of blinking the LED lamp 310 to send a signal to the user. The program may also perform a function of embodying the result value of the travel distance sensor 330 on the LCD display window 320.

Below a more detailed explanation will be given about the LED lamp 310 and the LCD display window 320. When the paracentesis needle reaches the epidural space, the LED lamp 310 emits light or flashes to inform the user of the correct position of the epidural space.

The LCD display window 320 serves the function of informing the travel distance of the medicine injection catheter 1000 injected into the epidural space through the inner space of the connection tube 500. After the epidural space is located, the medicine injection catheter 1000 needs to be inserted into the body to allow the injected medicine to reach the desired position. Therefore, the present invention may further have a sensor 330 for measuring the travel distance of the medicine injection catheter 1000 in order to accurately identify the travel distance and position of the medicine injection catheter 1000.

The principle of measuring the travel distance of the medicine injection catheter 1000 is preferably a noncontact type. In one example, if the user inserts the medicine injection catheter 1000, a laser sensor senses and calculates the travel distance, and then displays the result on the LCD display window 320, thereby allowing the user to easily identify the length of the catheter inserted into the human body.

Of course, it is obvious that a transparent window may be provided at a predetermined part of the connection tube 500 or that the connection tube 500 may be made of a transparent material, so that the travel distance of the medicine injection catheter 1000 can be perceived.

Meanwhile, the reset button 120 provided at a predetermined position of the upper case 100 is a button for initializing the measurement values when the measured pressure or travel distance is to be measured again.

A portable battery 600 is provided at the bottom of the connection tube 500 to supply power to all of the electrical devices inside the PCB substrate.

Hereinafter, a process of locating the epidural space and injecting a medicine using the detection device for recognizing the epidural space according to the present invention, which has the above constitution, will be described.

First, it is determined which part of the human body the paracentesis needle is to be inserted into in order to locate the epidural space, and then a spine needle or an epidural needle is selected accordingly.

The selected needle is coupled to the detection device of the present invention, specifically, one end of the connection tube 500, and the cap part 510 is fixed to the other end. Next, the power button 110 provided at a predetermined position on the outer surface of the upper case 100 is turned on to make the detection device for recognizing the epidural space ready for operation.

The needle is inserted via the designated area of the patient to detect the epidural space, with which the LED lamp 310 emits light. When the needle is positioned at the epidural space, the cap part 510 of the connection tube 500 is separated and the medicine injection catheter 1000 is inserted into a predetermined space part of the connection tube 500. Then, the medicine injection catheter 1000 is inserted up to a position determined by a preliminary examination by checking the travel distance of the medicine injection catheter 1000 displayed on the upper case 100, and the medicine is injected.

While the present invention has been particularly described with reference to specific embodiments thereof, those skilled in the art will appreciate that such specific embodiments are merely preferred embodiments and that the scope of the invention is not limited thereby. It will be apparent to those skilled in the art that various changes and modifications may be made without departing from the spirit and scope of the invention. It is obvious that such modifications and variations fall within the scope of the appended claims.

What is claimed is:

1. A detection device for recognizing an epidural space, comprising:
    an upper case having a predetermined shape; and
    a lower case coupled to the upper case to form a predetermined space part, where the lower case is removable from the upper case,
    wherein a connection tube is provided at a predetermined position of the predetermined space part, one end of the connection tube configured to couple with a paracentesis needle part and the other end of the connection tube having a detachable cap part, and an opening being provided at a predetermined position of an outer peripheral part of the connection tube, the opening communicating with a pressure sensor for measuring pressure,
    wherein the other end of the connection tube is configured to receive a medicine injection catheter when the detachable cap part is detached from the other end,
    wherein the upper case has fixing protrusions for fixing the paracentesis needle part, the lower case has a fixing groove part for fixing and accommodating the paracentesis needle part, and the predetermined space part further has a PCB substrate having a program embedded therein for calculating a result of the pressure sensor,
    wherein the fixing protrusions are protruded from the upper case toward the lower case,
    wherein the fixing groove part of the lower case fixes the paracentesis needle part, together with the fixing protrusions of the upper case, and
    wherein an outer expansion part is further removably provided on an outer surface of the one end of the connection tube to be connected to the paracentesis needle part.

2. The detection device for recognizing the epidural space according to claim 1,
    wherein the PCB substrate further has a LED lamp for indicating the calculation result of the pressure sensor.

3. The detection device for recognizing the epidural space according to claim 1,
    wherein the PCB substrate further has a travel distance sensor capable of sensing a travel distance of the medicine injection catheter.

4. The detection device for recognizing the epidural space according to claim 3,
    wherein the upper case is made of a diffusion PC.

5. The detection device for recognizing the epidural space according to claim 3,
    wherein the PCB substrate further has a LCD display window for informing a result of the travel distance sensor.

6. The detection device for recognizing the epidural space according to claim 5,
    wherein a power button and a reset button are further provided on one side of the upper case.

7. The detection device for recognizing the epidural space according to claim 6,
    wherein the one end and the other end of the connection tube protrude from the predetermined space part of the upper case and the lower case.

8. The detection device for recognizing the epidural space according to claim 7,
    wherein the outer expansion part is made of an elastic body.

* * * * *